(12) United States Patent
Weeks et al.

(10) Patent No.: US 11,993,761 B2
(45) Date of Patent: May 28, 2024

(54) INDOOR FOOD WASTE FERMENTATION AND RECYCLING PROCESS

(71) Applicant: RECYCLE TRACK SYSTEMS INC., New York, NY (US)

(72) Inventors: Amanda Weeks, Brooklyn, NY (US); Brett Van Aalsburg, Brooklyn, NY (US); Stephen Turek, Freehold, NJ (US); Emilie Benoit, Jr., Brooklyn, NY (US)

(73) Assignee: RECYCLE TRACK SYSTEMS INC., New York, NY (US)

( * ) Notice: Subject to any disclaimer, the term of this patent is extended or adjusted under 35 U.S.C. 154(b) by 0 days.

(21) Appl. No.: 18/011,519

(22) PCT Filed: Jun. 18, 2020

(86) PCT No.: PCT/US2020/038423
§ 371 (c)(1),
(2) Date: Dec. 19, 2022

(87) PCT Pub. No.: WO2021/257080
PCT Pub. Date: Dec. 23, 2021

(65) Prior Publication Data
US 2023/0242845 A1 Aug. 3, 2023

(51) Int. Cl.
*C11D 13/00* (2006.01)
*A23K 10/26* (2016.01)
(Continued)

(52) U.S. Cl.
CPC .......... *C11D 11/0094* (2013.01); *A23K 10/26* (2016.05); *A23K 10/37* (2016.05); *A23K 50/90* (2016.05); *C02F 9/00* (2013.01); *C05F 9/04* (2013.01); *C05F 17/20* (2020.01); *C05F 17/30* (2020.01); *C05F 17/40* (2020.01); *C05F 17/60* (2020.01); *C11D 7/261* (2013.01); *C11D 7/265* (2013.01); *C12N 1/20* (2013.01); *C02F 1/048* (2013.01); *C02F 1/32* (2013.01);
(Continued)

(58) Field of Classification Search
CPC ......... C11D 13/00; C11D 15/00; C05F 17/00; C05F 17/20; C05F 17/50; C05F 17/60; C02F 9/00; Y02W 10/00; Y02W 10/10; Y02W 30/20; Y02W 30/74
See application file for complete search history.

(56) References Cited

U.S. PATENT DOCUMENTS

| 10,588,331 B2 * | 3/2020 | Popa | A23K 10/12 |
| 11,220,467 B2 * | 1/2022 | Weeks | C11D 3/2086 |

(Continued)

*Primary Examiner* — Brian P Mruk
(74) *Attorney, Agent, or Firm* — Amardeep S. Grewal; Reed Smith LLP (57) ABSTRACT

The invention is a system and method for transforming food waste into a commercial cleaning product. The system is containable in an enclosed facility and installable in urban environments. Food waste is sorted and ground into uniformly sized particles, heated to an acceleration temperature, inoculated with an inoculant including lactic acid bacteria, which is mixed into the ground waste. The waste then undergoes sedentary fermentation for times as short as 24 hours or less. The fermented waste is separated into liquids and solids, and liquids are further separated into at least one distillation stream. Solids are dried to obtain a second distillation stream.

10 Claims, 6 Drawing Sheets

(51) Int. Cl.

| | |
|---|---|
| *A23K 10/37* | (2016.01) |
| *A23K 50/90* | (2016.01) |
| *C02F 9/00* | (2023.01) |
| *C05F 9/04* | (2006.01) |
| *C05F 17/00* | (2020.01) |
| *C05F 17/20* | (2020.01) |
| *C05F 17/30* | (2020.01) |
| *C05F 17/40* | (2020.01) |
| *C05F 17/50* | (2020.01) |
| *C05F 17/60* | (2020.01) |
| *C11D 7/26* | (2006.01) |
| *C11D 11/00* | (2006.01) |
| *C11D 15/00* | (2006.01) |
| *C12N 1/20* | (2006.01) |
| *C02F 1/04* | (2023.01) |
| *C02F 1/32* | (2023.01) |
| *C02F 1/44* | (2023.01) |
| *C02F 11/04* | (2006.01) |
| *C02F 11/13* | (2019.01) |
| *C02F 103/32* | (2006.01) |

(52) U.S. Cl.
 CPC ............... *C02F 1/444* (2013.01); *C02F 11/04* (2013.01); *C02F 11/13* (2019.01); *C02F 2103/32* (2013.01); *C02F 2301/046* (2013.01)

(56) References Cited

U.S. PATENT DOCUMENTS

| | | | |
|---|---|---|---|
| 2018/0194698 A1* | 7/2018 | Weeks | C05F 9/02 |
| 2022/0089506 A1* | 3/2022 | Weeks | C05F 17/50 |

* cited by examiner

INDOOR FOOD WASTE FERMENTATION AND RECYCLING PROCESS

CROSS REFERENCE TO RELATED APPLICATIONS

This application is related to U.S. Non-Provisional application Ser. No. 15/867,948, filed on Jan. 11, 2018, which claims priority to U.S. Provisional Appl. No. 62/444,929 filed on Jan. 11, 2017; and U.S. Provisional Appl. No. 62/517,094 filed on Jun. 8, 2017.

FIELD OF THE INVENTION

The invention lies in the fields of food waste processing by acidic fermentation and the manufacturing of products containing organic acids.

BACKGROUND

Anaerobic fermentation of carbohydrates is a well-known process for turning plant-based materials into organic acids and alcohol. Anaerobic fermentation is used in a wide variety of applications including beer and wine production, and the pickling and preservation of foods. Anaerobic fermentation relies on yeasts, bacteria, and other microorganisms, which process the organic matter into organic acids and alcohols. For instance, under suitable conditions, inoculation of *Saccharomyces* will produce ethyl alcohol, while *Lactobacillus* will produce lactic acid. Lactic acid fermentation is an ancient method for food preservation during which spoilage and pathogenic organisms such as yeasts, molds, enterobacteria, bacilli, and clostridia are inhibited by the conditions developed throughout fermentation, i.e. decrease in pH, low oxidation reduction potential, and competition for essential nutrients. Related fermentation processes have also been described for home use to process plant and animal-based waste into a soil fertilizer. For many reasons, not least because they require a lengthy fermentation period that would be inefficient for large volumes of waste, these processes have typically not been applied on a large scale.

Food waste is typically the largest component of urban solid waste streams, and all too often winds up in landfill. As landfill, the carbohydrate-rich nutrients from food waste enters the groundwater, contributing to acidification, algal blooms, and many other risks to human health. It would thus be desirable to have a means for recycling food waste that would reduce our landfill burden and reduce harmful effects on groundwater, and instead produce useful and safe byproducts.

While others have proposed recycling of food waste at larger scale, many focus on the production of methane because of its value as an energy source, and do not address the extended fermentation or digestion periods required. Methane production moreover emits noxious odors and greenhouse gases, and must therefore be built at some distance away from urban centers. It would be preferable to take a more sustainable approach and build solid waste treatment sites closer to sources of waste. For this to be palatable to municipalities, however, this approach would require drastic reductions in emissions of gases and odors. It would also be preferable for these urban treatment sites to be self-contained and easily replicable and scalable, for mass adoption.

SUMMARY

It is an objective of the invention to provide a scalable food waste recycling process capable of accepting large volumes of waste and treating and recycling the food waste within 7 days. It is another objective of the invention to treat and recycle the food waste in a manner that minimizes harmful byproducts and instead maximizes useful end products, namely by resulting in the production of energy, probiotic soil fertilizer, chemical and enzyme solutions, insect feed, organic acid solutions, purified water, and treated water. It is a further objective of the invention to minimize the energy requirement of carrying out this process, and to rely on byproducts from the process itself to fuel the process, rather than procure chemicals and materials from outside.

It is another objective of the present invention to provide a process that can be carried out in a relatively compact, contained facility that can easily be installed at the urban level in an enclosed environment, and for this process and any system to carry it out to be easily replicable and scaled. By way of example, it should be noted that it is not an objective of the present invention to produce methane, which would necessitate safe means for storage and transport, and would typically not be feasible to install in an urban environment. It is another objective of the present invention to limit wastes requiring disposal to non-food impurities such as plastics and metals, and a nominal quantity of treated liquid waste. It is a further objective to minimize greenhouse gases from being emitted.

In pursuit of these objectives, the invention is a process for recycling food wastes, including excess food, and other organic waste, comprising steps of: (1) intake and screening of food waste, including draining of free-flowing liquids and removal of observed plastics, metals and other undesirables; (2) reducing the food waste into uniformly sized particles; (3) accelerating fermentation of the reduced waste by raising its temperature to up to 45 degrees Celsius, and saturating the reduced waste with inoculant in a rotating or other mixing device for up to 48 hours; (4) fermenting the accelerated food waste without mixing until after it reaches pH of 4 or below, resulting in a fermented batch comprised of liquids and solids; (5) separating the liquids and solids; (6) further processing the separated liquids resulting in a first liquid stream; (7) drying the solids, simultaneously collecting a fermentation distillate during the drying process, resulting in a second distillate from the drying of said wet solid; (8) combining and processing the first and the second distillate resulting in commercially usable products, in particular a cleaning solution product; and (9) processing the dried solids resulting in one or more treated solid byproducts.

Further processing of both the distillate from solids drying and further processed separated liquids results in a variety of marketable products including formulations for use as household cleaning agents, pure and mixed solutions of Acetic Acid, Ethanol, Lactic Acid and other organic acids, Ethanol and organic esters, treated water, high purity water, energy in the form of current or hydrogen, fertilizer, insect feed, animal feed, and other products. Different product outcomes depend on the types of input materials, inoculants used, base parameters, processing steps applied, and process equipment such as types of filters used to concentrate solutions.

DETAILED DESCRIPTION OF THE INVENTION

The following description refers to the accompanying drawings. Whenever possible, the same reference numbers are used in the drawings and the following description to refer to the same or similar elements. While embodiments of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. The proper scope of the invention is defined by the claims, and therefore the following detailed description does not limit the invention but serves to give further description to the claims.

The invention is a process for processing food wastes, including excess food which might not be normally categorized as food wastes, and other organic waste, particularly from and within an urban environment. The type of materials that can be processed using this invention will hereinafter be referred to as "food waste" or "waste" but can include any type of organic waste, whether derived from food or not, including, but not limited to, excess or unconsumed food, garden waste and debris, animal feed, etc. . . . . However, the process described herein generally contemplates the processing of urban food waste that would be generated, for example, by restaurants, businesses, schools, households and food processing facilities.

I. Intake and Screening

Figure 2:
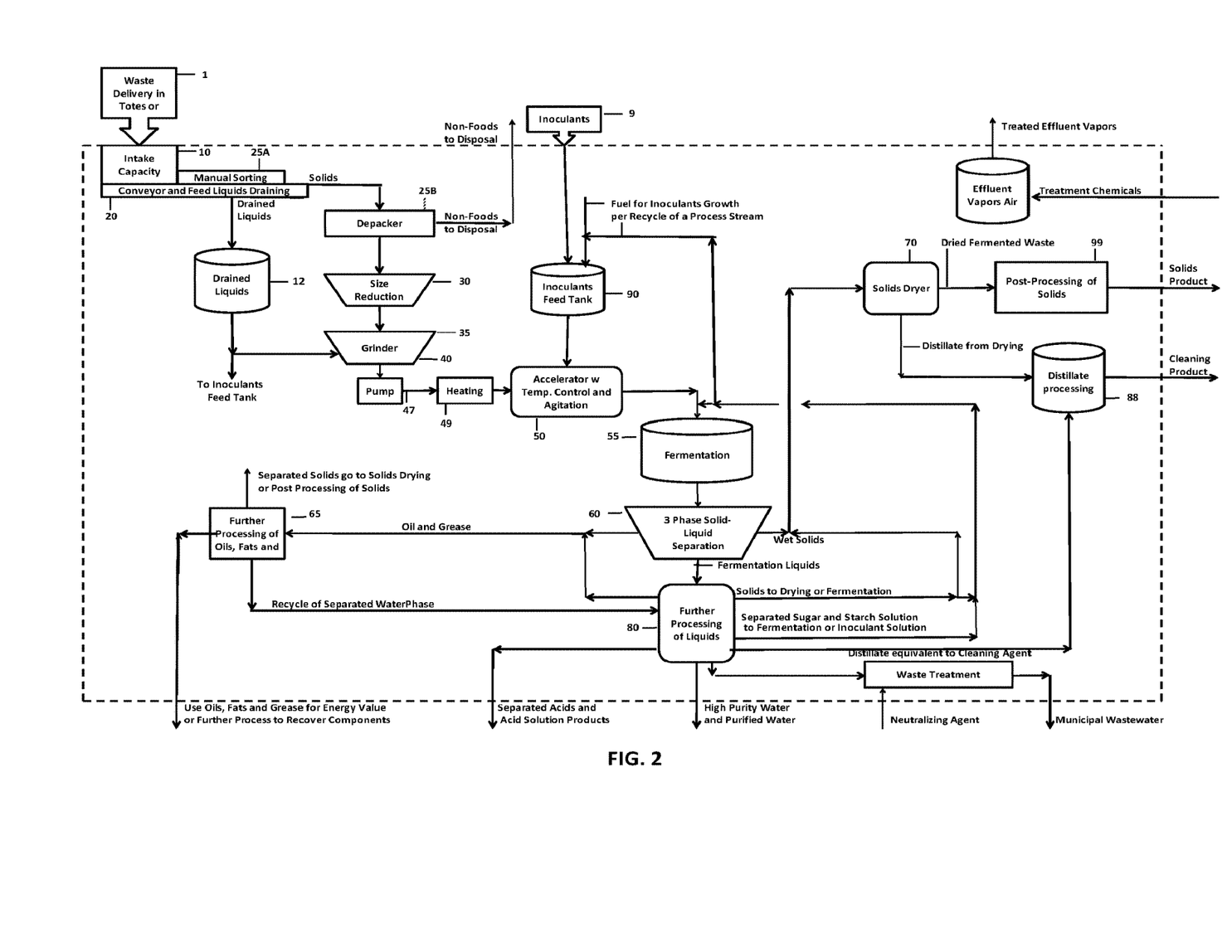
FIG. 2 is a schematic diagram illustrating an exemplary food waste recycling system.

Preferably, the process can be carried out by a single closed system, installable in an enclosed facility that could be located in a wide variety of urban settings while remaining compliant with municipal laws and regulations, such as those that govern the distance of such facilities from homes or buildings, or their output of odors and noxious emissions. The system schematic of FIG. 2 shows the elements of such a system, installable in an enclosed facility.

Figure 1:
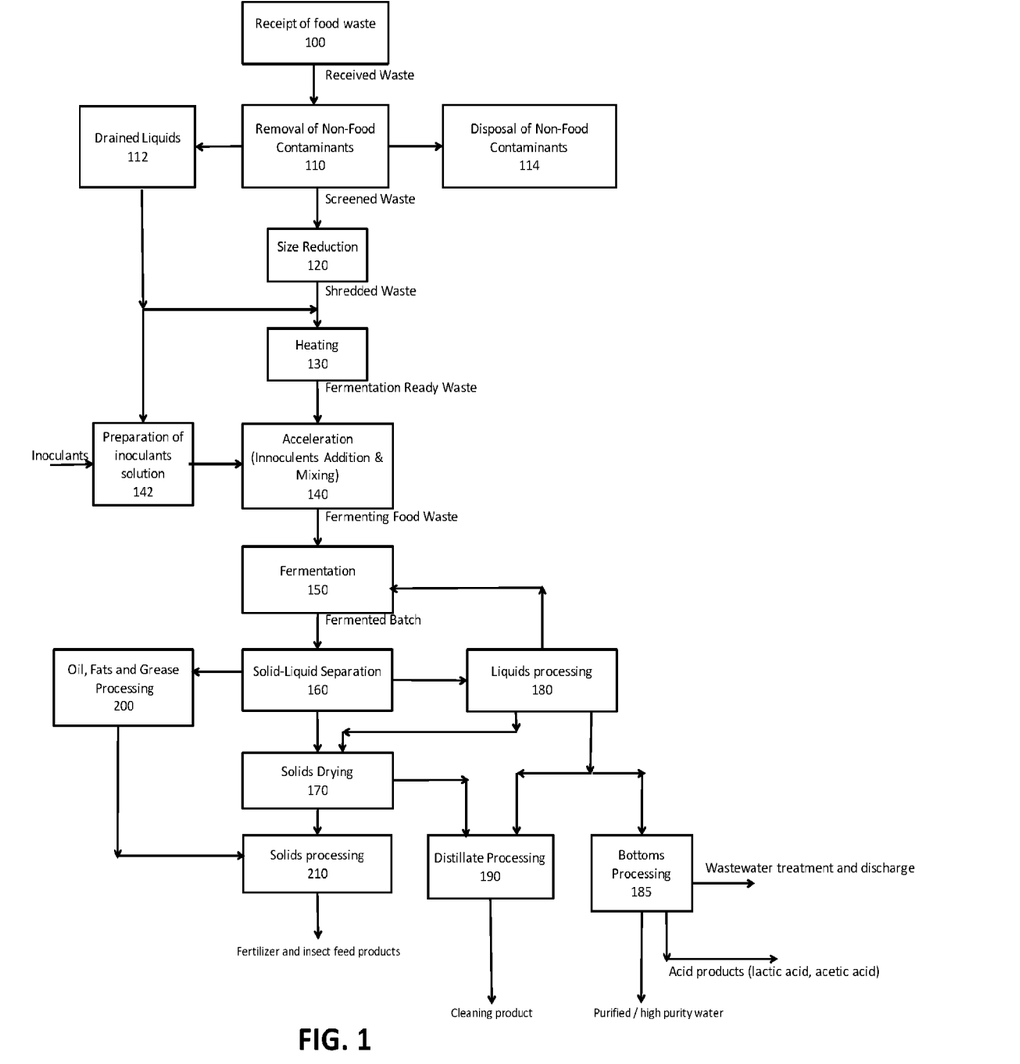
FIG. 1 is a process flow chart.

Food waste is received [100] from haulers at an intake unit [10]. Preferably, smaller quantities of food waste are transported in containers specifically designed for the transportation of food waste. Upon receipt [100], the food waste containers can be weighed and inspected. One or more parameters associated with the food waste, for instance, weight, food waste type, source, and/or pH, can be logged for further study towards tailoring of operations towards specific products.

Receiving step [100] may also comprise facilitating and analyzing the collection of food waste from city dwellers, restaurants, schools, businesses and industrial food waste sources. Each customer that sends waste to the facility will use food waste collection containers marked with a tracking number. After the bins are deposited at the facility by waste haulers, their contents are scanned and analyzed at intake unit [10]. The intake unit may use computer-aided tracking to associate the composition of a bin with the tracking number and thus the customer. Intake unit [10] may be equipped with a monitoring camera which provides a visual record of all materials received. The video records can provide fuller details on the intake materials, can be used to separate materials and can provide information useful in the design of subsequent systems. Materials can also be inspected while being unloaded at the intake point.

As the daily processed waste volume increases, bulk dumping trucks become a more efficient delivery means. These trucks will be a dumping or other suitable design. Preferably they are capable of lifting totes at the source, dumping their contents into the truck's hauling compartment, compressing the materials to reduce their volume, primarily by the elimination of air which gives size and volume, and emptying the contents into the processing site's receiving pits. All unloading will be inside a facility building to insure maximum odor control at all times. Bulk trucks can be weighed before and after unloading, and load parameters logged.

After receiving step [100], removal [110] of non-food contaminants is performed. The accepted food waste is fed forward from the intake point using a conveyor system [20] that is enclosed to contain odors. Unwelcome components such as cutlery, cups, napkins, or other non-food and non-organic wastes are initially removed in a gloved sorting area [25A]. This gloved sorting area [25A] comprises a food grade conveyer contained within a containerized glove box enclosure, which enables screening to be performed by hand through gloves that can reach into the interior of the enclosure and access the contents on the conveyer. The purpose of enclosed removal is to reduce odors and promote a clean and sterile facility environment.

As an increasing volume of processed material requires the use of bulk trucks, the sorting area [25A] will simply remove larger plastic and metal items, and a downstream depacker [25B] or equivalent can remove additional undesired feed materials. A depacker is a specialty piece of equipment which combines the internal compression, pounding and forward pushing of feed materials to force the food wastes to separate by exiting through bottom rain holes. Items which do not come apart (i.e. paper, most plastics) and larger items (i.e. metals) exit through a backend screw discharge. The depacker internal drain holes are along its bottom with a size design to give optimal performance for the specified operation. A combination of automatic and manual screening components, as per described for the processing of materials from containers, will remove larger plastic bags and other items which could interfere with the operation of the depacker [25B]. The collected non-food contaminants can be transmitted [114] for further recovery by others or for disposal.

Screening may also be automated and can be performed by computerized methods, including but not limited to, sensors, magnets, color and shape analysis, size-based, vibration, x-ray, air currents, weight-based, air knife apparatus, or advanced optical screeners. Generally, only inorganic items are removed, but removal does not need to be limited to nonorganic waste and in some cases may be used to remove organic elements. For instance, some organic elements may be deemed too large for the process or unsuitable for acidic fermentation. Removal step [110] results in a screened waste that can be conveyed forward to size reduction step [120].

Moving floors along the bottom of larger waste receipt pits will move the wastes to outlet points which feed solids conveyors [20]. Liquids naturally draining from the received and sorted wastes will drain [112] into a receiver [12] where they can be held for further use downstream. For instance, these liquids may be used in size reduction step [120], in which operation of depacking [25B] and/or size reduction equipment [30], [40] is facilitated by lubrication. They may also be used in the preparation [142] of inoculants solution, where they are used as a feed source for inoculants [90], as further described in Section IV.

Example 1—Intake and Screening

In one example, (1) receive materials directly from generators, primarily cafeterias and food services, in 64 gallon totes; (2) totes weighed and inspected, with top contents being noted, upon receipt); (3) totes re-batched based upon observed contents; (4) totes dumped using devices which lift and dump them into a bin with a bottom exiting conveyor; (5) most larger non-organics, to include the plastic tote liners, are separated at the dumping point; (6) liquids, which freely separate, drain into a vessel under the system's sorting conveyor; (7) solids from the receiving bin are conveyed thru an isolation tunnel with three manual sorting points; (8) sorters manually remove observed non-organic materials, with the exception of some smaller materials such as fruit labels; (9) sorters take out some more difficult to process items, such as shells and larger whole fruits, so they can be processed with greater scrutiny; and (10) the outlet of the sorting convey feeds directly into the inlet of a shredder.

II. Size Reduction

The screened waste is next reduced [120] to uniformly sized particles. Screened waste is first shredded by industrial shredding blades [30], or a suitable alternative. This shredding may be followed by a cross shredding [35] (or equivalent process) to address the elongated shape of a single shredder pass and to obtain uniform sized materials. The size reduction will preferably produce a waste size no larger than one-eighths (⅛) inches in spherical diameter.

In an embodiment, the shredded screened waste drops from the conveyer into grinder [40] or other suitable size reduction device. Grinder [40] is operable to further reduce the waste to a small, uniform particle size, preferably a maximum of ⅛ cubic inch spherical diameter. Said size reduction device may be an industrial waste disposal grinder, shredder or equivalent device. Preferably the grinder is fed by a covered hopper that receives the conveyed material, controlling the flow rate and any potential particle emissions. A combination of size reduction steps, which may include shredding and grinding steps, enables the adaptation of currently existing machinery to efficiently result in the desired particle size.

Alternative means for reducing the size of the screened waste may be implemented without departing from the spirit of the invention. For instance, some embodiments may use an industrial shredder comprising shearing blades for generally reducing the size of the waste, and the waste may be batched and transmitted to a grinder without using a conveyer apparatus. Depending on the size reduction achieved, a subsequent size reduction step may be needed downstream in order to further process certain solid byproducts.

Where batching is implemented, it may be necessary to utilize holding tanks in order to accumulate sufficient volumes and maximize throughput. Nor does the reduction [120] of screened waste into uniformly sized particles need be performed in two sequential steps, and instead may be accomplished in a single step using custom made cutting machinery or by a second size reduction step somewhere downstream.

Depending on the means used, the reduction step may require additional lubrication. In particular, a small amount of water may be introduced to aid in grinding and also enables the ground waste to be pumped instead of conveyed. Lubrication can also be facilitated by the addition of liquids that accumulate in other steps in the process. For instance, liquid that was drained [112] from the intake materials, liquid resulting from fermentation, or liquid resulting from the size-reduction step itself may be used to lubricate the reduction step. In some embodiments, shredded waste can be connected to a holding tank in which accumulated shredded waste is batched before pumping to heater [49] and accelerator [50].

Example 2—Size Reduction

Materials from a sorting conveyor (1) feed directly into a shredder in which they are reduced to strips of roughly ⅛ to ¼ inch diameter (but sometimes result in more complicated shreds due to the adhesive nature of feed materials); (2) feed into the hopper and screw feed of a progressive cavity pump; and (3) have the collected drained liquids batched back into the shredded materials at the pump's hopper inlet.

III. Heating and Acceleration

After size reduction step [120], the shredded waste is heated [130] and accelerated [140]. Heating step [130] and acceleration step [140] may occur simultaneously or separately. During heating step [130], the waste is heated to a maximum acceleration temperature of 45° C. to prime the waste for fermentation. The acceleration temperature can be higher than optimal fermentation temperatures, which can range from 34 to 40° C., since heating [130] may be applied first followed by acceleration [140] without further application of heat. In some cases, depending on the temperature to which it is heated and the time it remains at said temperature, heating to higher temperatures to pasteurize or sterilize the waste may be desirable to eliminate pathogens. Pasteurization temperatures can range from 60 to 80° C., with ideal pasteurization temperature of the shredded waste being 76° C. Methods of heating, pasteurization or sterilization include, but are not limited to, UV, steam pasteurization, heating by flow through heat exchangers and freezing. Heating [130] can be performed by a heat exchanger [49]. Other methods include circulation of a heated fluid, liquid or gas, convectively on the tank's surface using a heating element or by recirculation the material to be heated through sections of jacketed pipe. Other heating embodiments may use outlet temperature control of steam injection into a recirculation pipe or vessel, fermenter jackets, heat tracing or electric heating blankets.

Acceleration step comprises the mixing [140] of fermentation-ready waste with inoculants solution at or above a fermentation temperature in order to distribute the inoculant and accelerate the fermentation. Temperatures of 34 to 40° C. are found to be optimal for fermentation. Overheating can have deleterious effects on inoculant microbes but adding some inoculants earlier in the process—even as early as size-reduction—to cause early microbe growth may compensate for potential loss of microbes caused by overheating. Thus, if heating [130] exceeds fermentation temperatures, then temperature should be allowed to reduce before the addition of the bulk of the inoculants.

Acceleration time can be very short. Acceleration [140] can be applied for up to 48 hours but will likely only require a fraction of that time to accomplish adequate acceleration before non-agitated fermentation [150] begins. Rotation for 36-48 hours at 37° C. is found to accelerate the subsequent fermentation step, but the process does not require a minimum acceleration period to be effective. For instance, the shredded waste can be inoculated, brought to 37° C. while being rotated for one hour or less, or it can be brought to a higher temperature such as 76° C. for pasteurization, allowed to cool to 37° C., inoculated, then rotated for one hour or less. Acceleration step is sufficiently short so as to make extended temperature control unnecessary, whether or not separated from the heating step [130].

Acceleration [140] can be performed by a continuously stirred tank reactor (CSTR) [50], an industrial agitator or other physical method. Alternatively, acceleration may utilize recirculation (in some cases with a static mixer) or may be accomplished by bottom feeding through inoculant solution or by use of gravity. For instance, one method is to feed the heated waste into the bottom of an unagitated accelerator, which is either a vessel or pipe, and overflow out of the top. The rising and floating of the bulk of solids will maintain their flow through the vessel while the liquid will overflow from a filled vessel. The vessel will be sized to provide sufficient residence time to more than adequately soak all materials passing through with inoculants.

When heating [130] and acceleration [140] are combined, the heater/accelerator may comprise an industrial incubator such as a rotary mixing tank within a large enclosure that comprises an electrical heat source below the rotary mixing tank and an air input source for the convection of hot air over the surface of the tank as it rotates. As another example, the accelerator may comprise a jacketed mixer with internal mechanical mixing means and an inlet for heated gas to enter the mixer. In embodiments using heated gas mixing with the food waste, said heated gas can be re-circulated $CO_2$ produced by anaerobic fermentation in fermenter [55], which is already maintained at an optimal fermentation temperature. Furthermore, in the aforesaid embodiment, the addition of $CO_2$ is an efficient means of displacing oxygen and speeding up anaerobic fermentation. Sensors can be used to monitor temperature and pH.

Example 3—Heating and Acceleration

After size reduction, (1) feed the outlet of the progressive cavity pump to a chain of jacketed pipe heat exchangers, using hot water at up to 82.2° C., to heat the waste; (2) feed the outlet of the heat exchangers into the bottom of coned bottom fermentation vessels; (3) subsequently recycle the contents of the fermentation tanks through the pipe heat exchangers, using another progressive cavity pump, until the desired fermentation temperature is attained; (4) add the required quantity of inoculants solution as a batch to the fermentation tanks; and recirculate the fermentation tanks until the inoculants solution is thoroughly mixed into the batch.

IV. Inoculants Solution Preparation

The inoculants are a mixture of organisms selected from, by way of example, Lactic Acid bacteria, *Lactobacillus plantarum, Lactobacillus casei, Lactobacillus fermentum, Lactobacillus delbrueckii, Bacillus subtilis, Saccharomyces cerevisiae*, and/or *Rhodopseudomonas palustris*. The mixture of organisms in the inoculant can vary and comprise other organisms.

The inoculants grow in a liquid inoculant solution, which may be prepared [142] and stored in a dedicated tank [90]. Microbes can be preserved by drying if the vessel is not needed. Separate tanks may also be used for different inoculants solutions, with parameters such as food source, temperature and water content being varied to optimize performance for each desired product mixture. Preferably the tank is agitated and maintained at the specified fermentation temperature to ensure its contents are ideal for use. Outlet from the tank is fed directly to the accelerator [50]. Fresh inoculants organisms should be added as maintenance of minimum organism feed levels require.

One way to minimize the addition of purchased inoculants is by periodically adding food source to the inoculants solution. The addition of a food source results in inoculant microbe multiplication. Food sources for the inoculants solution can come from liquid drained [112] from intake [10] and diverted to the inoculants tank [90], from other downstream food sources where sugars and starches remain unreacted, or from the addition of external food sources such as molasses. The tank acts as a backmix reactor by enabling sufficient residence time for the growth of inoculants, and sufficient capacity to avoid feeding all its contents into the process. A tank capacity double the normal daily throughput rate would give a 24 hour average residence time for the growth of microbes. The presence of a vessel agitator would increase the efficiency of the process. The inoculants solution can be monitored for pH, temperature, time since preparation and microbe concentration to determine when fresh feed is required.

Example 4—Inoculants Solution Preparation for Pilot Operations

Pilot operations have prepared inoculants solution using a non-agitated vessel. The process involves (1) charging a food source, such as molasses, for microbe growth to the tank; (2) adding Lactic Acid bacteria to the vessel; (3) allowing the bacteria to grow; and (4) batching materials from the tank to the fermentation tanks while maintaining sufficient volume in the vessel for future batches. If the vessel sits unattended for a length of time addition of fresh microbes and food may be necessary.

V. Anaerobic Fermentation

After acceleration, the accelerated waste undergoes sedentary anaerobic fermentation [150]. It may remain in the accelerator [50] or can be transferred to a fermentation tank [55] for fermentation [150]. If fermentation tanks [55] are used separate from accelerator [50], the volume of material to be processed plus fermentation periods of up to seven days would require additional fermentation tanks for each day fermenting materials will remain in them.

Fermentation [150] throughout the vessel starts when all solids have been soaked with inoculants solution. Due to the acceleration step [140], anaerobic fermentation [150] can occur relatively quickly and without requiring further mixing within a sealed fermenter [55]. Accelerated food waste within fermenter [55] undergoes anaerobic, acidic fermentation [150] until a pH of 4 or below is reached. Due to acceleration step [140], further temperature control is not required, since the fermenter is sealed resulting in minimal heat loss to the ambient surroundings. However, internal sensors may be used to monitor data such as pH and temperature, and further temperature control may be performed. Fermentation to reach the desired pH may take up to 120 hours, but normally takes no more than 24 hours. Fermentation time can depend on factors such as the composition of the deposited food waste, the variety of inoculants used, and the length of time the screened food waste undergoes acceleration [140]. Due to the mixing and temperature optimization performed by the accelerator, this process does not necessarily require additional agitation, mixing by recirculation or rotation during fermentation in order to achieve results in an efficient timeframe.

During fermentation [150], the inoculant microbes added during the acceleration step [140] excrete organic acids as they consume sugars and nutrients present in the organic material. These organic acids dramatically lower the pH of the fermenting waste, causing pathogens to be unable to survive when maintained at a pH less than 4 for a sufficient time. In addition, this process creates an environment inhospitable to methanogens, suppressing methane generation in the anaerobic environment. Another factor in avoiding methane generation is the rapid fermentation time.

Depending on the inoculants used, the primary reaction occurring during fermentation of organic waste may be described by the following equation, where one mol of glucose is converted into one mol of lactic acid, one mol of ethanol, and one mol carbon dioxide. This type of fermentation is called heterolactic fermentation (commonly called lactic acid fermentation).

$$C_6H_{12}O_6 \longrightarrow CH_3CHOHCOOH + C_2H_5OH + CO_2$$
(glucose) (lactic acid) (ethanol) (carbon dioxide)

As seen in the above reaction, no methane is produced during lactic acid fermentation. End products of heterolactic fermentation include organic acids such as lactic, acetic, and propionic acid, making their growth environment unfavorable for the growth of many pathogens and spoilage bacteria. Organic acids are thought to function as antimicrobials by interfering with the maintenance of cell membrane potential, inhibiting active transport, reducing intracellular pH, and inhibiting a variety of metabolic functions. Thus, the process results in byproducts that do not require further pasteurization or treatment. However, in some embodiments, heat sterilization or other sterilization treatments may be applied here or at other points in the process, without departing from the overall process of the invention.

Another outcome of anaerobic fermentation is the breakdown of cell walls of the organic matter, releasing the high concentration of water present in food waste. This results in the separation of solids and liquids. The resultant fermentation batch settles into a top oil and grease phase, a lower water phase with floating solids, and heavier solids which settle to the bottom. The heavier solids which settle are most likely materials that do not ferment. The majority of solids float in and on top of the oil phase plus in the top of the water phase. Smaller solids float as suspended and colloidal solids in the water phase and possibly the oil phase. Emulsified oil and grease is found throughout the water phase included within suspended particles. The primary suspended solids behavior appears to be colloidal, which is attributed to the build-up of negative charges on the solids and grease and oil, in large part due to the lack of agitation during fermentation [150].

Example 5—Anaerobic Fermentation

After a fermentation batch is heated to the specified fermentation temperature and the inoculants solution has been mixed into it and accelerated, the batch is allowed to sit for at least 3 days until solid-liquid separation occurs. Since batches are normally started on a Thursday and solid-liquids separation occurs the beginning of the next week batches sit for at least 4 to 5 days before solid-liquid separation.

Fermentation measurements include pH and temperature. Samples are taken and analyzed as the fermentation proceeds. An absence of vessel heating normally results in a slow vessel temperature drop during fermentation. The fermentation reaction is mildly exothermic, which balances some loss of heat to the ambient surroundings.

VI. Solid-Liquid Separation

The result of anaerobic fermentation step [150] is a fermented waste comprising a top oil and grease phase, a lower liquid phase with floating solids, and heavier solids which settle to the bottom. These phases can be separated in a solid-liquid separation step [160], which can occur at any time once fermentation has commenced. For instance, solid-liquid separation [160] can be applied to parts of the fermented waste that are withdrawn from fermenter [55] prior to full completion, potentially reducing the fermentation tank load and maximizing acid production. Output from solid-liquid separation are wet solids, to be further processed by drying [170], fermentation liquids with floating solids further processed in a liquids separation step [180], and/or oil and grease further processed in oil and grease processing step [190]. These will be discussed further in Sections VII, VIII and X.

Separation [160] can be performed by active or inactive means, including passive draining, centrifugal screener, vibratory drain filter, hydraulic press, belt filter press, decanter centrifuge, tricanter centrifuge, bowl centrifuge, cross-flow filter, etc. . . . , or combinations of the foregoing. For instance, separator [60] may comprise a vibratory drain filter that uses a mechanical sifting movement to separate the solids and liquids, or a tricanter centrifuge to separate all three phases. It is also feasible to decant or filter separately the top oil and grease phase to include solids it contains.

Solids within the liquid are colloidal due to the build-up of ion charges around particles resulting in mutual repulsion of particles. The forces also act to fight the normal settling of the particles due to mutual repulsion of the suspended keeping them suspended. The non-agitated nature of the fermentation facilitates a higher build-up of negative charges around particles. Suspended solids plus oil in the water phase bind fine filtration paths, which limits the initial solid-liquid separation [160] equipment to items without fine mesh screens. The high liquid-solids content of the fermented batch means that this initial separation step [160] may focus primarily upon separating the heavy solids from the liquids and oil and grease to facilitate subsequent processing of the liquids.

Example 6—Initial Solid-Liquid Separation

This example uses a combination of a Vibrating Filter and a Screw Press for the initial Solid-Liquid Separation. The initial solid-liquid separation steps are (1) feed the entire contents of the fermentation batch to the vibrating filter; (2) collect separated liquids from the vibrating filter in a receiver; (3) feed effluent solids from the vibrating filter to the screw press; (4) collect liquids from the screw press into a receiver and (5) collect solids from the screw press in a manner that prepares them for subsequent drying. When this method is applied, the split of materials is roughly 30% as the liquid from the Vibrating Filter, 30% as the liquid from the Screw Press and 40% as the wet solids from the Screw Press. Either a recycle of liquids or use of flush water may be used to get all the solids out of the fermentation vessel.

The split and characteristic of the separated stream are resultant from the set-up characteristics of the used filtration equipment. The vibrating filter has a reasonably open screen that results in the pass though liquids containing up to 20% solids although the normal level is 10%. Tests with a 45 micron filter resulted in fouling of the filter and almost no pass through of materials. The binding of the 45 micron screen is comparable to that reported for filtration tests and is attributed to the combined presence of colloidal and suspended solids plus both the oil and grease layer, and emulsified oil and grease.

The screw press screen is finer than that of the vibrating filter with the pass though liquids containing up to 20% solids although the normal level is 10%. The normal operation of a screw press can mechanically force solids through its filter screen. The solids from the screw press average 75% liquids based upon the subsequent separation of materials during drying. Alternate screw press configurations can reduce the liquids content.

VII. Solids Drying

Fermented food waste solids are dried [170] to remove moisture. Distillate from drying step [170] is a valuable byproduct that can be further processed, as described in Section IX. Resulting dried solids are also a valuable byproduct that can be further processed, as described in Section XI. Fermented food waste solids fed to solids dryer [70] for drying [170] may come from the initial solid-liquid separation [160] or secondary liquids separation step [180]. Before or after drying, the solids may be inspected to remove small contaminants that remain in the fermented waste.

Solids dryer [70] may be a fluid bed dryer, which introduces hot air or gas upward through a bed of solid fermented waste. Another embodiment may utilize a heat source in combination with convective drying by an airflow. In some embodiments, the heat source is infrared in order to minimize energy use. Other known drying apparatuses may be used without departing from the spirit of the invention. Drying can be performed for any period of time, but is preferably performed until the solid fermented food waste loses at least 50% of its weight. In other embodiments, a relative humidity sensor can be used as a metric to indicate dryness when the humidity in the heating apparatus begins to drop.

Solids dryer [70] also comprises a condenser in order to collect the distillate. After vapor has been removed by distillation, air flow may be reheated and recirculated through the dryer. To produce solids products which contain fermentation microbes and Lactic Acid, the drying and distillation conditions need to take into account the destruction of microbes that starts above 48.9° C. and the decomposition of Lactic Acid that starts at 65.5° C. The preferred approach to dry and recover evaporate are through keeping the hot drying air temperature sufficiently low so as to not overheat the solids being dried. Vacuum distillation is the preferred method for distillate collection, because boiling can be reached at lower temperatures and constant temperature can be maintained. Other approaches to recover distillate include the use of membranes, including reverse osmosis.

Example 7—Drying and Distilling Pilot Operation

Solids from the screw press are (1) placed on filter screen frames; (2) placed into the dryer; and (3) dried using a heated air feed into the bottom of drying boxes which contain the filter screen frames with the wet solids. The screens are stacked using side supports. The dried air passes upward through the frames, leaves the drying boxes and goes to a condenser where the distillate is condensed (4). The cooled air goes to a heater and the process repeats until the solids are at the specified level of dryness. (5) After drying the contents of the screen are often inspected to pick out small pieces of plastic and (6) the solids are deposited into a drum.

VIII. Further Processing of Separated Liquids

Figure 3:
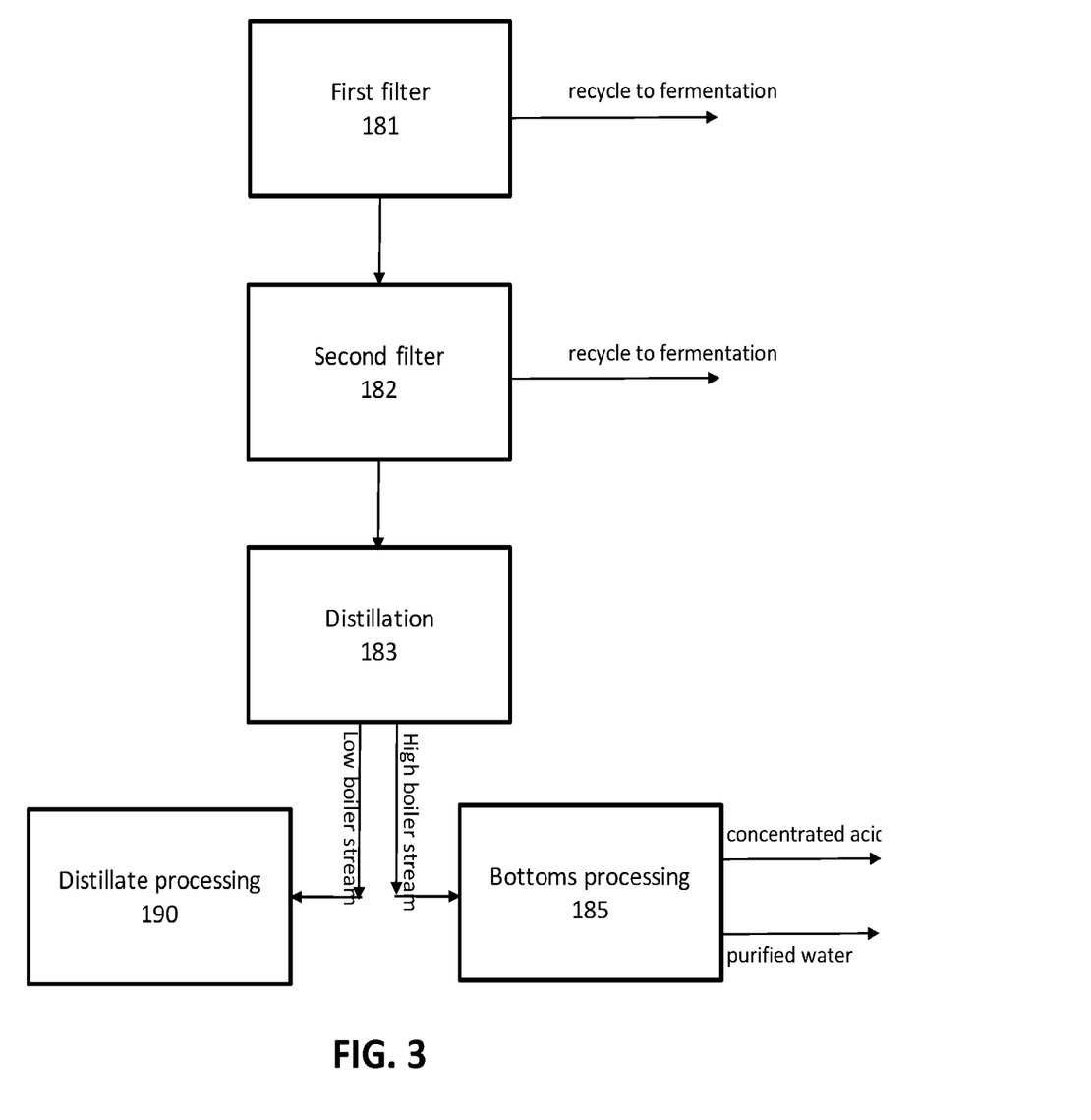
FIG. 3 is a flow chart showing detail of processing step [180].

Due to the separated liquids containing suspended colloidal solids plus oil phase emulsions, further processing of separated liquids [180] is performed in order to break particulate and colloidal suspensions and remove solids, and to concentrate organic acids in the water phase. Further processing of separated liquids step [180] may comprise (a) separation of the solids, oils, fats and grease by temperature or pH variation or settlement, followed by decanting or other removal method; (b) using a cross-flow filter to eliminate final traces of solids and potentially large molecules, such as sugars and starches; (c) using reverse osmosis membranes to split materials based upon size and ionic characteristics, with embodiments yielding separation of sugars, starches, organic acid, cleaning agent components, Ethanol and water; (d) distilling filtered retentate; (e) further processing distillate bottoms to separate and concentrate acids, purify water and separate impurities for treatment and disposal to a municipal wastewater system; and combinations of the foregoing. Further processing of separated liquids step [180] results in a highly refined first liquid stream that is further processed in distillate processing [190] to produce the cleaning product and purified water.

To some extent, the degree of further processing is determined by the output of the initial solid-liquid separation step [160]. For instance, if all three phases of oil, fats and grease, liquid with suspended solids, and heavy solids are separated at the solid-liquid separation step [160], such as by means of a tricanter centrifuge, then (a) further separation of oils, fats and grease is redundant. Otherwise, oil, fats and grease can be separated at further processing step [180], for instance by coalescer [66], settlement, centrifuge, or application of filters.

Figure 4:
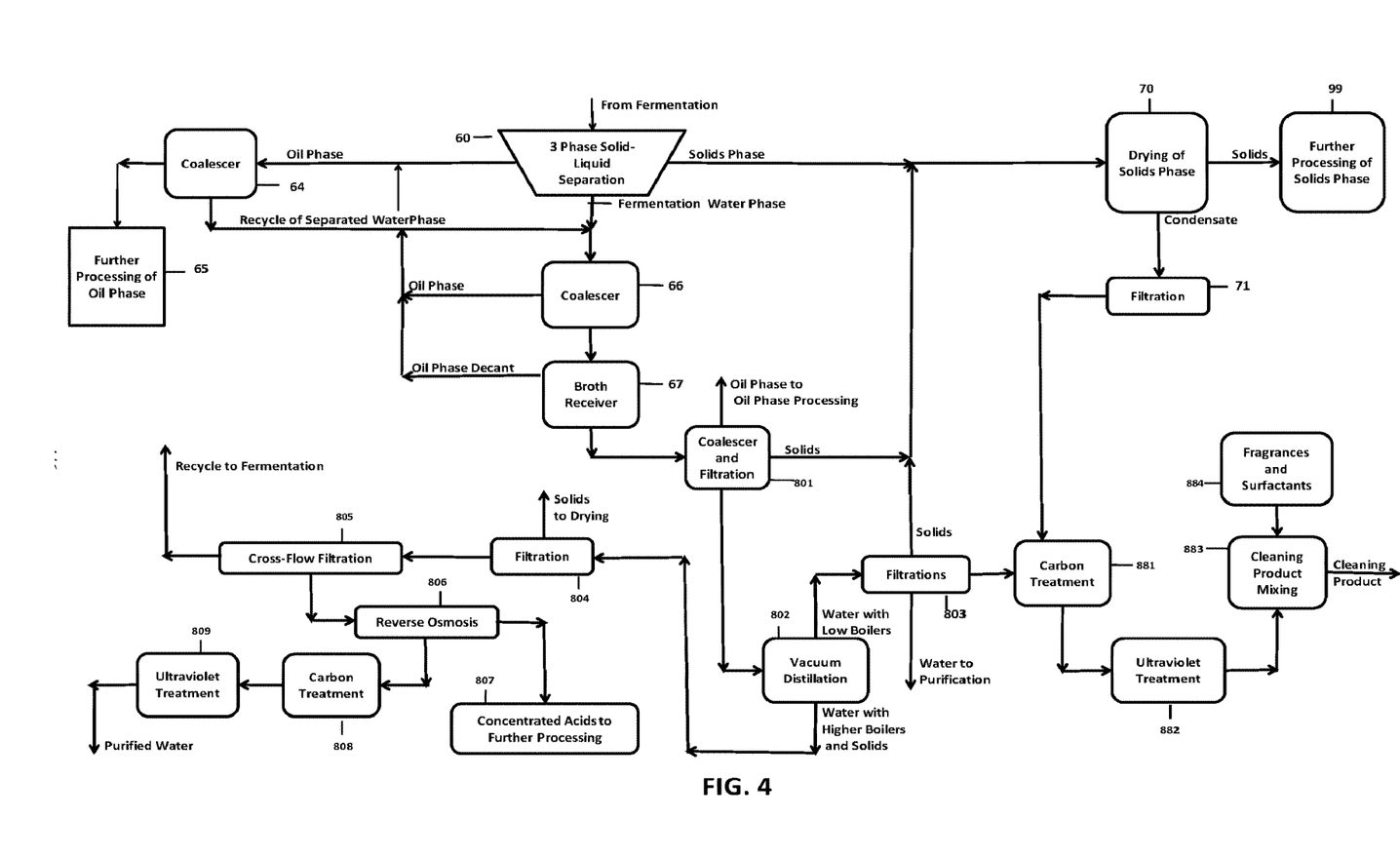
FIG. 4 is a schematic diagram illustrating details of liquid processing in a food waste recycling system.
Figure 5:
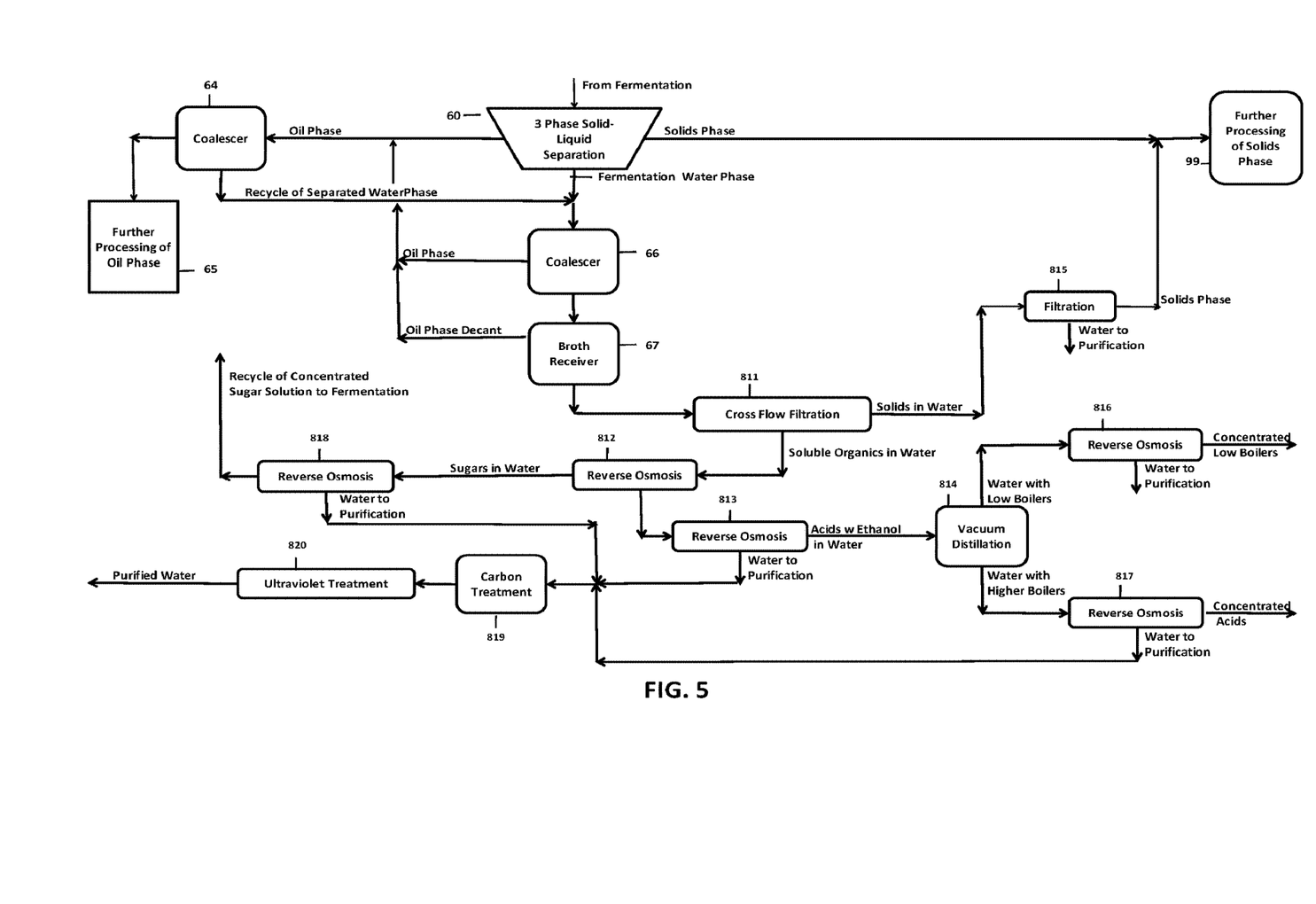
FIG. 5 is a schematic diagram illustrating details of liquid processing in a food waste recycling system.

Further processing step [180] may comprise a first filtration [181] performed on the liquids after the oils, fats and grease have been removed, followed by vacuum distillation [183] to result in the first liquid stream used for distillate processing [190]. The first filtration may be by cross-flow filtration [811] or any other appropriate filter [801]. The pore sizes of membranes, including cross-flow and reverse osmosis, separate components based upon their molecular sizes combined with the pressure required to push compounds through the membranes. Adding a charge to a membrane can enable separation based upon ionic charge. This gives a variety of options to apply in choosing membranes while not precluding the use of other approaches, such as distillation, to separate materials. Care must be taken due to the possibility of the materials fouling or plugging the membranes. Further processing step [180] may make use of this variety of options. For instance, the application of cross-flow filtration [811] produces a clean clear water permeate containing soluble compounds plus a retentate containing separated solids and compounds, including sugars and starches, which have not passed through the membrane. Multiple filters may be applied, for instance, further processing step [180] may comprise a first filtration [181], such as application of cross-flow filter [811], followed by a second filtration [182], such as application of reverse osmosis filter [812], before distillation [183] of the permeate of the second filtration [182]. Retentates containing sugars and starches may be recycled for additional fermentation [150]. Retentates may also contain concentrated bacteria and microbes, which may be recycled to the inoculants solution tank [90]. The application of further processing steps [180] may be adjusted based on the end products that are sought. FIGS. 4 and 5 both show details of exemplary systems for carrying out further processing step [180].

Vacuum distillation [183] is used to further process and separate. Liquids with low boiling points, derived when the evaporator is operated at pressures between 0.15 to 0.7 psi, comprise a first distillation stream. The first distillation stream primarily comprises acetic acid, ethanol and water. This first distillation stream becomes the first liquid stream that can be further processed [190] into a cleaning solution as discussed in Section IX. Liquids with higher boiling points and solids comprise a second distillation stream, or bottoms, which is further processed [185] to produce a purified water from the permeate, while retentate is a concentrated acid solution with potential commercial value. This retentate is primarily comprised of lactic acid, with smaller quantities of acetic acid, sugars (glucose, sucrose, fructose), ammonia, nitrate and ethanol. The second distillation stream may be processed [185] using a variety of filters, as described above, to yield separated bottoms products including purified water, organic acid solutions, sugar and starch solutions and a solution of impurities. Organic acid solutions containing lactic acid concentrations of at least 10%, and acetic acids of at least 6% have been achieved using these methods. Side streams from water purification will be recycled or treated as necessary for discharge to a municipal wastewater system.

Example 8—Additional Separated Liquids Processing

The following example method can be performed by the system shown in FIG. 5: (1) process the broth to remove colloidal solids, such as via coalescer [66], (2) filter to minimize solids and retain broth [67], (3) feed the filtered broth through a cross-flow filter to obtain a clean solution, (4) feed clean solution through a sequence of reverse osmosis membranes [812], [813] to first separate soluble organics (retentate) from acids (permeate) and then produce concentrated acids (retentate) and purified water (permeate); and (5) perform a high vacuum evaporation on the concentrated acids retentate to recover a distillate containing water, acetic acid, ethanol and some minor components. The collected distillate is sent for further processing as described in Section IX.

IX. Distillate Processing

Distillate from solids drying step [170] and further liquids separation step [180] is an aqueous solution composed primarily of water and approximately 1.16% of purified organic acids and ethanol. Depending on the composition of the waste that was received and processed, the composition of the distillate per part water was found to be within the following ranges: Acetic Acid: 0.37-0.61%; Ethanol: 0.12-0.5%; Lactic Acid: 0.0086-0.031%; Butanoic acid: 0.01%; Formic acid: 0.005%; Propionic acid: 0.005%. In particular, lactic acid, acetic acid and ethanol have disinfectant and antibacterial properties and can be found in conventional and green cleaning products such as floor cleaners, window cleaners, surface cleaners, and hand sanitizers. The presence of contaminants in both distillates requires distillate processing [190] to ensure their purity for consumer sale. Contaminants can include particulates, bacteria and liquids from entrainment. The distillate processing [190] is for the purpose of making safe for commercial sale and may include a combination of filtration, carbon absorption and ultraviolet treatment.

Example 9—Further Processing of Distillate to Cleaning Product

Distillate is (1) processed through a sequence of dead-end cartridge filters starting at 50 microns and processing downwards through several filters to 0.2 micron filtration. This is followed by (2) feeding the distillate through an activated carbon filled cartridge; (3) ultraviolet light treatment; and (4) the addition of fragrances and surfactants to make the cleaning product. Filtration removes particulates and microbes. Carbon Treatment removes odors and selected chemicals. Ultraviolet light treatment destroys bacteria and pathogens which reach that point. Fragrances mask undesired odors. Surfactants are required to solubilize the fragrances.

X. Processing Separated Oils, Fats and Grease

The oil, fats and grease phase after separation from broth contains solids, emulsified water with organics, and organics which are soluble in the oils phase. Oils, fats and grease processing step [200] may include (1) filtration to separate solids, (2) feeding through a coalescer to remove water phase droplets, (3) cooling and filtration to separate materials that solidify and (4) selling oil phase for its fuel value or mixing the oil phase into recovered solids for sale as part of animal feed, insect feed and fertilizer products.

Example 10—Processing of Oil, Fats and Greases

Oils, Fats and Grease which separates with the solids phase remain after additional processing to become part of the solids products. During drying light boilers can evaporate. The evaporated low boilers either are condensed to become part of the distillate or vent to an air treatment system. Oil phase which remains in the water phase split during evaporation between the bottoms and evaporation. The majority remains in the condensate due to the evaporator design. Some light boilers exhaust during distillation or evaporate after. Some oil phase is stored in barrels.

XI. Post-Processing of Dried Fermented Waste

Figure 6:
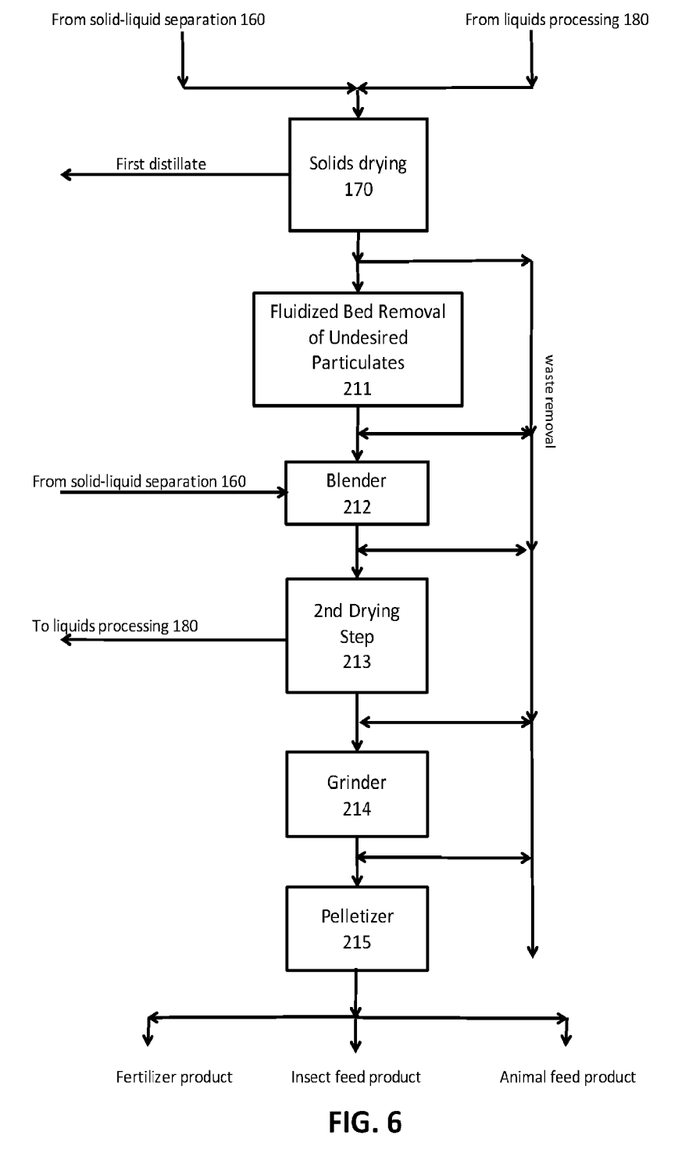
FIG. 6 is a process flow chart showing detail of solids processing.

The remaining dried fermented waste comprises a treated solid that is shelf-stable, pathogen free, and usable as fertilizer or insect or animal feed. It also contains an array of macro and micro nutrients, and organic acids which provide a natural pesticide effect. In particular, the presence of concentrated lactic acid produces a superior fertilizer product. Due to the microbial fermentation process, in which pH is reduced to 4 or below, further pasteurization or treatment is not required for the dried fermented waste to be shaped and used in consumer and commercial applications. Thus, the function of solids processing step [210] is to process and shape the solid waste for consumer and commercial use. This step may comprise several sub-steps, including removing [211] undesired particles using a fluidized bed, blending [212] the dried waste with liquids and/or recovered oil, fats and grease phase, drying [213] the blended waste, grinding [214] the dried, blended solid waste into smaller particles, and [215] pelletizing the ground and blended material. As a result, the solid waste is condensed into products such as cakes, pellets, or flakes. This step is performed in one or more solids processing units [99] that include hydraulic pressers, pelletizers, extruders, or even further drying units.

Example 11—Further Processing of Dried Solids to Produce Pellets

Pellet-shaped fertilizer product is produced via a process that (1) grinds the ground dried solids into smaller more uniform particles; (2) adds liquid to the ground dried solids and blending (per added liquids being required to make pellets) and (3) feeding the materials to a pelletizer where they are formed into pellets. Drying may be required if excess liquids are added to the solids.

XII. Optimizing Output by Altering Parameters

As detailed herein, the present invention yields an array of useful end products, from electricity to fertilizer. Yields of these useful end products can be optimized as desired, including in response to real time data pertaining to the composition of the food waste that was collected during intake or at some other point in the process, such as by testing holding tank batches. Fermentation products and yields may be altered by varying such parameters as: the composition of the inoculant; the length of time in either the accelerator or the fermenter; and the temperature of either the accelerator or the fermenter. For instance, lactic acid yield is maximized when the food waste is accelerated at a temperature of 37° C. Lactic acid bacteria is used in the inoculants solution when the desired end result to be maximized is the cleaning product.

In another example, where the production of hydrogen is desired to be maximized, pretreatment applied in the accelerator should have the purpose of maximizing the concentration of simple sugars for the utilization of hydrogen producing micro-organisms. In this example, accelerator temperature has been found to be optimal between 30° C. and 50° C., and the inoculant applied should at least comprise Enterobactericae and Clostridiacease. Process parameters, such as the adjustment of water content, may be modified to maximize the production of glucose from complex carbohydrates.

The invention claimed is:

1. A process for producing a cleaning solution from food waste comprising the steps of:
    removing inorganic items from the food waste, resulting in a screened waste;
    reducing the screened waste into uniform particles, resulting in a shredded waste;
    heating the shredded waste to up to 45 degrees Celsius;
    applying an inoculants solution containing lactic acid bacteria to the shredded waste and mixing the shredded waste with the inoculant for up to 48 hours, resulting in a fermentation-ready waste;
    fermenting the fermentation-ready waste until pH reaches 4 or below, resulting in a fermented batch;
    separating the fermented batch into a liquid and a wet solid;
    further processing the liquid to remove suspended particles resulting in a first liquid stream;
    drying the wet solid using heat until the wet solid achieves 50% or greater reduction in weight, resulting in a dried fermented waste;
    collecting condensate from the drying of the wet solid resulting in a second liquid stream; and
    processing the first and the second liquid streams together by applying up to 0.2 micron filtration and ultraviolet light treatment resulting in the cleaning solution.

2. The process of claim 1 wherein the inoculants solution is stored in an inoculant holding tank and comprising additional steps of
    draining free-flowing liquids from the food waste;
    monitoring the inoculants solution for sugars concentration; and
    adding the free-flowing liquids drained from the food waste to the inoculant holding tank before sugars concentration reaches zero.

3. The process of claim 1 wherein the further processing of the liquid step comprises applying a first filter followed by distilling a permeate of the first filter, resulting in the first liquid stream.

4. The process of claim 2 wherein the further processing of the liquid step comprises applying a first filter followed by distilling a permeate of the first filter, resulting in the first liquid stream.

5. The process of claim 1 wherein the further processing of the liquid step comprises applying a first filter and a second filter, recycling a retentate of the first or the second filter to fermentation, and distilling a permeate of the second filter, wherein distilling a permeate of the second filter results in the first liquid stream.

6. The process of claim 2 wherein the further processing of the liquid step comprises applying a first filter and a second filter, recycling a retentate of the first or the second filter to fermentation, and distilling a permeate of the second filter, wherein distilling a permeate of the second filter results in the first liquid stream.

7. The process of claim 3 wherein distilling a permeate of the first filter comprises a first distillation stream from low boiling point liquids and a second distillation stream from high boiling point liquids, wherein the first liquid stream is equivalent to the first distillation stream, and further comprising the step of applying a third filter to the second distillation stream, resulting in a concentrated acid solution and a purified water.

8. The process of claim 4 wherein distilling a permeate of the first filter comprises a first distillation stream from low boiling point liquids and a second distillation stream from high boiling point liquids, wherein the first liquid stream is equivalent to the first distillation stream, and further comprising the step of applying a third filter to the second distillation stream, resulting in a concentrated acid solution and a purified water.

9. The process of claim 5 wherein distilling a permeate of the second filter comprises a first distillation stream from low boiling point liquids and a second distillation stream from high boiling point liquids, wherein the first liquid stream is equivalent to the first distillation stream, and further comprising the step of applying a third filter to the second distillation stream, resulting in a concentrated acid solution and a purified water.

10. The process of claim 6 wherein distilling a permeate of the second filter comprises a first distillation stream from low boiling point liquids and a second distillation stream from high boiling point liquids, wherein the first liquid stream is equivalent to the first distillation stream, and further comprising the step of applying a third filter to the second distillation stream, resulting in a concentrated acid solution and a purified water.

* * * * *